United States Patent
Yu et al.

(10) Patent No.: US 11,439,689 B2
(45) Date of Patent: Sep. 13, 2022

(54) METHOD FOR DETECTING WHETHER GLUCOSE METABOLISM IS ABNORMAL, AND PREVENTION AND TREATMENT THEREFOR

(71) Applicant: KAOHSIUNG MEDICAL UNIVERSITY, Kaohsiung (TW)

(72) Inventors: Ming-Lung Yu, Kaohsiung (TW); Wan-Long Chuang, Kaohsiung (TW); Jee-Fu Huang, Kaohsiung (TW); Chia-Yen Dai, Kaohsiung (TW); Yu-Min Ko, Kaohsiung (TW)

(73) Assignee: Kaohsiung Medical University, Kaohsiung (TW)

( * ) Notice: Subject to any disclaimer, the term of this patent is extended or adjusted under 35 U.S.C. 154(b) by 463 days.

(21) Appl. No.: 16/349,286

(22) PCT Filed: Nov. 14, 2016

(86) PCT No.: PCT/CN2016/105759
§ 371 (c)(1),
(2) Date: May 13, 2019

(87) PCT Pub. No.: WO2018/086126
PCT Pub. Date: May 17, 2018

(65) Prior Publication Data
US 2020/0093897 A1    Mar. 26, 2020

(51) Int. Cl.
*A61K 38/44* (2006.01)
*C12N 15/85* (2006.01)
*A61P 3/10* (2006.01)

(52) U.S. Cl.
CPC .............. *A61K 38/44* (2013.01); *A61P 3/10* (2018.01); *C12N 15/85* (2013.01)

(58) Field of Classification Search
CPC .................... C12Y 111/01009; A61P 3/10
See application file for complete search history.

(56) References Cited

FOREIGN PATENT DOCUMENTS

| CN | 104651329 A | 5/2015 |
|---|---|---|
| WO | WO2006056080 A | 6/2006 |
| WO | WO2006056080 A1 | 6/2006 |

OTHER PUBLICATIONS

Roberts et al. 2009; Oral administration of glutathione peroxidase mimic SYI-2074 ameliorates post-MI heart failure in type 1 diabetes mellitus. Journal of Cardiac Failure 15(6): Supplement S3, Abstract 031.*

Sasongko et al. 2019; Effect of orally administered glutathione peroxidase mimetic towards glutathione and malondialdehyde blood level and otoacoustic emissions results in soldiers with acoustic trauma risk caused by Howitzer 105 artillery weapon blast. Asian Journal of Applied Sciences 7(1): pp. 1-14.*

Bhowmick et al. 2015; Insights into the catalytic mechanism of synthetic glutathione peroxidase mimetics. Organic & Biomolecular Chemstry. 13: 10262-10272.*

Poitout et al. 2006; Regulation of the insulin gene by glucose and fatty acids. J. Nutr. 136(4): 873-876.*

Hammerstad SS, Greek SF, Lee HJ, Hasham A, Sundaram N, Tomer Y. Diabetes and Hepatitis C: A Two-Way Association. Front Endocrinol (Lausanne). Sep. 14, 2015;6:134.

Hammerstad SS, Greek SF, Lee HJ, Hasham A, Sundaram N, Tomer Y., Diabetes and Hepatitis C: A Two-Way Association. Frontiers in Endocrinology (Lausanne). Sep. 14, 2015, vol. 6, Article 134.

* cited by examiner

*Primary Examiner* — Karen Cochrane Carlson
(74) *Attorney, Agent, or Firm* — Hannah M Tien

(57) ABSTRACT

A method for detecting whether glucose metabolism is abnormal comprises: detecting GPx2 gene expression, GPx2 protein expression or the activity of GPx2 protein in a test body, and making comparisons with GPx2 expression amount of a normal individual, when the GPx2 expression of the individual is significantly lower than that of the normal individual, indicating that the carbohydrate metabolism of the individual is in an abnormal state. Applications of GPx2 in the preparation of a medical composition for the treatment and prevention of type II diabetes.

3 Claims, 15 Drawing Sheets
(4 of 15 Drawing Sheet(s) Filed in Color)

A

B

A

B

A

B

METHOD FOR DETECTING WHETHER GLUCOSE METABOLISM IS ABNORMAL, AND PREVENTION AND TREATMENT THEREFOR

CROSS-REFERENCES TO RELATED APPLICATIONS

This patent application is a U.S. National Stage Application of PCT/CN2016/105759, filed on Nov. 14, 2016, which is incorporated herein by reference in their entirety.

FIELD OF THE INVENTION

The present invention is related to a method for detecting carbohydrate metabolism disorder by using glutathione peroxidase 2 (GPx2), and an application for use in the field of preventing and treating type II diabetes.

BACKGROUND OF THE INVENTION

Along with the change in eating habits, the diabetes prevalence has been risen year by year globally, and complications of diabetes have become one of the significant causes of death in human. Recently, there is a lot of evidence showing that the hepatitis C virus is one of the risk factors for diabetes, and can accelerate and increase the risk of developing diabetes in patients.

Diabetes is a growing problem worldwide. Currently, there are no effective drugs to prevent diabetes. In respect of treatment, although there are hypoglycemic drugs which limitations on their uses. Some medications have limited efficacy; some are prone to cause complications related to hypoglycemia.

Patients suffering from chronic hepatitis C often have abnormally high blood glucose levels. Sometimes the patients even cause diabetes, but the cause of this phenomenon has not been clarified. Possible causes include activation of the TNF-α system, fatty hepatocytes or fibrotic hepatocytes, leading to insulin resistance, etc. Previous studies have shown that insulin resistance is associated with the progression of hepatitis C, particularly the degree of liver fibrosis. In the case of treating hepatitis C using interferon combined with Ribavirin, the insulin resistance of the patient before treatment has been confirming as one of the critical indicators for predicting the success of the treatment. On the other hand, if the hepatitis C virus is eliminated, the insulin resistance, the function of pancreatic islet β-cells, and the expression of insulin receptors in the liver can be improved. Therefore, the hepatitis C virus should play a crucial role in insulin resistance and the development of type II diabetes. Exploring this role and its mode of actions will be helpful in understanding the pathogenic mechanism of diabetes and further identify the targets for the prevention and treatment of diabetes.

Accordingly, the present invention develops a target for preventing and treating diabetes by regulating genes and related factors based on hepatitis C leading to abnormal blood glucose metabolism of a host.

DESCRIPTION OF THE INVENTION

Either hepatitis C virus infection or a high-fat diet will cause a decrease in the expression of GPx2, to decrease in glucose uptake capacity of hepatocytes and to increase in gluconeogenesis in hepatocytes, which causes an increase in blood glucose level leading to diabetes. Taking advantage of a genetic network analysis software, it is finding that GPx2 is closely related to fatty acid oxidation, glucose tolerance, glucose uptake, and gluconeogenic genes. Since hepatic insulin resistance and an increase in hepatic gluconeogenesis are important pathogenic mechanisms of type II diabetes, the present invention uses the expression of liver GPx2 as a new target for preventing and treating diabetes without causing side effects of hypoglycemia.

Accordingly, the present invention provides a method for detecting carbohydrate metabolism disorder of a subject, comprising detecting the expression of GPx2 gene (DNA or RNA), the expression level of GPx2 protein, or the activity of GPx2 of a sample from the subject; and comparing to the expression level of GPx2 of a normal subject, wherein a significantly lower expression level of GPx2 in the subject than the expression level of GPx2 in the normal subject indicates that the subject is in a state of carbohydrate metabolism disorder. In particular, carbohydrate metabolism disorder is a state that the blood glucose concentration is higher than a normal range. Therefore, the present invention uses GPx2 as a marker for carbohydrate metabolism disorder.

The present invention further provides an use of GPx2 for preparing a pharmaceutical composition for treating and preventing type II diabetes. When GPx2 is given at the beginning of a high-fat diet, the expression of gluconeogenesis-related proteins is decreased, and the expression of GLUT (glucose transport protein) is increased. Therefor GPx2 has the efficacy of preventing type II diabetes. Administration of GPx2 after type II diabetes induced by a high-fat diet can also decrease the expression level of gluconeogenesis-related proteins and increase the expression of GLUT. Therefore GPx2 has the efficacy of treating type II diabetes.

The "sample" described herein is collected from a biological subject, wherein the sample is selected from the group consisting of tissue, feces, urine, cell homogenate, blood, serum, plasma, one or more biological fluids, and any combination thereof. The subject described herein is an animal, comprising a human and a mammal. Preferably the subject is a human.

The method of the present invention is particularly suitable for high-risk groups of type II diabetes, such as overweight people, activity-averse people, family factors (for example, one of parents or siblings are type II diabetes patients), ethnic factors, and aging people (especially those who are over forty-five year old), people having pre-diabetes (pre-diabetes is blood glucose value in the body is higher than normal, but insufficient to be classified as type II diabetes, if not controlled, it will develop into Type II diabetes), or those who have had gestational diabetes.

It can be learned from the examples of the present invention that in the liver cells having hepatitis C virus protein expression (hepatitis C virus replicons), the expression level of GPx2 is decreased, the cellular glucose uptake is also decreased, and the gluconeogenesis is significantly increased. Through the administration of anti-hepatitis C virus drugs (such as Daclatasvir) to inhibit the hepatitis C virus protein, or through transfecting plasmids that overexpress GPx2 to increase the expression level of GPx2, the cellular glucose uptake is effectively increased, and gluconeogenesis is decreased.

The metabolic mechanism affected by GPx2 can be observed through hepatocytes having no hepatitis C virus replicons and normal expression of GPx2, by transfecting GPx2 siRNA to downregulate the expression of GPx2. It can be learned from the results that addition of GPx2 siRNA can decrease the expression of GPx2, and at the same time affect insulin signaling pathways, reduce glucose uptake by the hepatocytes, and significantly increase gluconeogenesis in the hepatocytes. As shown in FIG. 15, FIG. 15A shows that the expression of GPx2 is inhibited in Huh7.5 cells treated with GPx2 siRNA, and a decrease in the expression level of GPx2 is detected by Western blotting. The expression levels of GLUT1 (glucose transporter protein 1) and GLUT2 (glucose transporter protein 2) also are decreased; the expression levels of PEPCK and G6PC (G6Pase) in the cells are also significantly increased (FIG. 15B). The increase in gluconeogenesis in the hepatocytes is one of the important factors leading to diabetes. Accordingly, GPx2 plays a key role in regulating glucose metabolism by the hepatocytes. Hepatitis C virus induces type II diabetes by affecting the expression of GPx2 in the hepatocytes to cause abnormal glucose metabolism of a host. Therefore, by correcting or enhancing the low expression of GPx2 in hepatocytes, abnormal glucose metabolism can be effectively restored in the hepatocytes.

Through constructing a GPx2 over-expressing plasmid and administering the plasmid into the mice with a high-fat food via tail vein injection, the effect of GPx2 on blood glucose is observed. It can be found from the results that, as compared to the mice having normal expression of GPx2, an increase in gluconeogenesis in the mice administered with the GPx2 over-expressing plasmid in early stage can be significantly prevented, the abnormal glucose metabolism and blood glucose control are effectively improved, thereby reducing the risk of suffering from diabetes. In addition, when the diabetic mice having abnormal glucose metabolism induced by a high-fat food are treated by administering the GPx2 over-expressing plasmid, the condition of the abnormal glucose metabolism can be effectively improved to achieve the purpose of controlling blood glucose. As shown in FIG. 3B, after a high-fat food successfully induces diabetic mice for 16 weeks, the GPx2 over-expressing plasmid is administered via tail vein injection, abnormal carbohydrate metabolism is effectively improved over 32 weeks. The above results confirm that hepatic GPx2 plays a vital role in affecting blood glucose regulation; correcting or enhancing the expression of hepatic GPx2 can effectively improve abnormal glucose metabolism, thereby achieving the purpose of controlling blood glucose. Therefore, GPx2 not only prevents diabetes but also achieves therapeutic effects when diabetes has already developed.

The composition of the present invention is suitable for being used as organic or inorganic carriers or excipients for enteral or parenteral administration. For example, active ingredients may be combined with, non-toxic, and pharmaceutically acceptable carriers usually used in tablets, pills, capsules, suppositories, solutions, suspensions, and any other suitable forms of carriers. The carriers which may be used comprise glucose, lactose, arabic gum, gelatin, mannitol, starch paste, trisilicate, talc, corn starch, keratin, colloidal silicon oxide, potato starch, urea, medium chain triglycerides, dextran, and other carriers suitable for preparing solid, semi-solid or liquid form of formulations. Also, adjuvants, stabilizers, thickening agents, colorants, and spices can also be used.

The composition of the present invention may be in a form suitable for oral administration, for example, as tablets, lozenges, sugar tablets, aqueous or oily suspensions, loose powder or granules, emulsions, hard or soft capsules, or syrups, or elixirs. Compositions or mixtures for oral administration can be prepared according to any methods known in the art of preparation of pharmaceuticals.

The pharmaceutical compositions of the present invention may also be sterile injectable suspensions. The suspensions can be formulated according to known methods using suitable dispersing agents, wetting agents and suspending agents. The sterile injectable solutions can also be sterile injectable solutions or suspensions prepared with non-toxic, gastrointestinal acceptable diluents or solvents.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

EXAMPLES

Cell Experiments

Figure 1A:
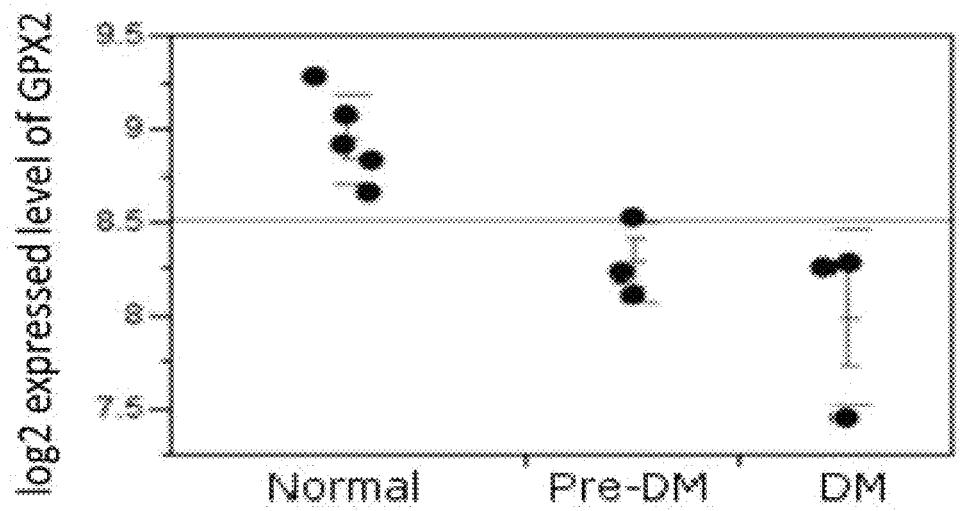
FIG. 1 shows the expression level of GPx2 Log 2 protein analyzed by qPCR; 1A: the expression level of GPx2 of the abnormal glucose tolerance group; 1B: the expression level of GPx2 of the validation group.

Huh7.5 and Huh7.5/Con1 cell replicons (genotype 1b) were cultured in a Dulbecco's Modified Eagle's medium (DMEM) with a high concentration of glucose, incubated in a 5% carbon dioxide/37° C. incubator, and supplemented with 10% heat-inactivated fetal bovine serum (heat-inactivated FBS), 5% antibiotic-antimycotic solution, 100 U/mL penicillin, 100 μg/mL streptomycin, and 5% non-essential amino acid solution. The cell lines were first subjected to starvation treatment for 24 hours, then fresh medium containing 10% FBS and annonacin was added and in vitro experiments were performed. The Con1 cell lines were continuously cultured in a complete medium (containing 0.5 mg/mL of G418).

Immunoblotting

A 30 μg sample of cytolysate was placed on a 10% SDS-polyacrylamide gel, electrophoresis was performed, and transfected to a PVDF membrane. After being blocked, the membrane was separately immersed in a solution containing the target protein GPx2, GLUT1, PCK1 (PEPCK), GLUT2, and G6PC (G6Pase) antibodies (primary antibody), and incubated for two hours, and then washed with PBS containing 0.1% tween 20 for five minutes. Subsequently, the membrane was incubated in the HRP complex secondary antibody for one hour. An enhanced chemiluminescence reagent (ECL) was applied on the membrane for light irradiation to observe the protein distribution.

Plasmid Construction and Transient Transfection

The cells were placed in a six-well plate medium in the amount of $1.2 \times 10^5$ cells per well and allowed to grow for one night. The GPx2 over-expressing plasmid and siGPx2 (GPx2 siRNA) were transfected to the cells using LipofectAMINE® at a specifically specified period of time. In addition, the vehicle was only transfected with pcDNA (a vehicle) or siNC (control siRNA) and served as the control group.

Animal Experiments 24 weeks: The mice were fed with a high-fat food to induce abnormal glucose metabolism: six-week-old C57BL/6 male mice were kept in a pathogen-free environment for two weeks. All mice were then randomly divided into six groups, at least five mice in each group. Group 1 was fed with normal food; group 2 was fed with normal food, and the plasmid carrier (50 μg/plasmid/mouse/week, dissolved in Turbofect) was injected once a week via the tail vein of the mouse; group 3 was fed with normal food, and the GPx2 over-expressing plasmid (50 μg/plasmid/mouse/week, dissolved in Turbofect) was injected once a week via the tail vein of the mouse; group 4 was fed with food having 30% more fat than normal food; group 5 was with fed with a food having 30% more fat than normal food, and the plasmid carrier (50 μg/plasmid/mouse/week, dissolved in Turbofect) was injected once a week via the tail vein of the mouse; group 6 was fed with a food having 30% more fat than normal food, and the GPx2 over-expressing plasmid (50 μg/plasmid/mouse/week, dissolved in Turbofect) was injected once a week via the tail vein of the mouse. All mice were sacrificed after 24 weeks, their tissues were collected and divided into three parts: the first part was fixed with 4% formaldehyde and embedded in paraffin for a tissue section study; the second part of the tissues was stored in a tissue RNA sample preservation solution (RNAlater) and placed in an −80° C. environment for subsequent gene expression detection; the third part of the tissues was stored in liquid nitrogen.

48 weeks: Six-week-old C57BL/6 male mice were kept in a pathogen-free environment for two weeks. All mice were then randomly divided into four groups, at least five mice in each group. Group 1 was fed with normal food; group 2 was fed with a food having 30% more fat than normal food; group 3 was fed with a food having 30% more fat than normal food, and the plasmid carrier (50 μg/plasmid/mouse/week, dissolved in Turbofect) was injected once a week, 16 weeks after the mice began to be fed in the experiment, via the tail vein of each mouse; group 4 was fed with a food having 30% more fat than normal food, and the GPx2 over-expressing plasmid (50 μg/plasmid/mouse/week, dissolved inn Turbofect) was injected via the tail vein of each mouse once a week, 16 weeks after the mice began to be fed in the experiment. All mice were sacrificed after 48 weeks, their tissues were collected and divided into three parts: the first part was fixed with 4% formaldehyde and embedded in paraffin for a tissue section study; the second part of the tissues was stored in a tissue RNA sample preservation solution (RNAlater) and placed in an −80° C. environment for subsequent gene expression detection; the third part of the tissues was stored in liquid nitrogen.

For those mice fed with high-fat food to induce abnormal glucose metabolism, the expression level of hepatic GPx2 was significantly decreased.

Figure 2:
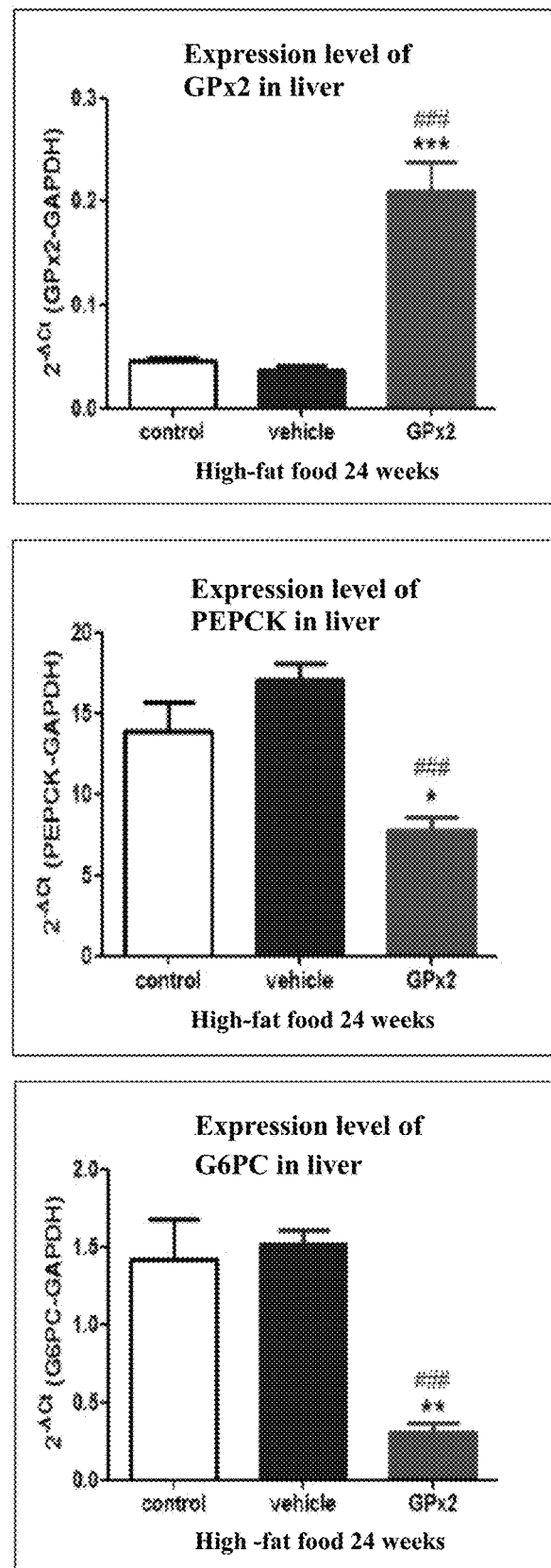
FIG. 2 shows the expression level of GPx2, PEPCK, and G6PC (G6Pase) in the livers of the mice fed with a high-fat food for 24 weeks and calculated by using the $2^{-\Delta\Delta CT}$ method (compared to GAPDH, presented by folds) (compared to the control group, *:p<0.05; : p<0.01; *: p<0.001; compared to the vehicle, ###: p<0.001).

For those mice feed with a high fat food and simultaneously administered with the GPx2 over-expressing plastid via the tail vein, it was found by qPCR detection that the expression of GPx2 in the liver of the mice having the GPx2 over-expressing plastid was significantly increased and the expression of the genes (PEPCK and G6PC (G6Pase)) related to gluconeogenesis was effectively decreased, as shown in FIG. 2.

Glucose Tolerance Test (GTT)

All mice were fasted for 12 hours and injected intraperitoneally with glucose (2 g glucose/kg body weight), followed by blood sampling from the tail at 0, 30, 60, and 120 minutes after the glucose injection. The blood glucose meter was used to detect blood glucose concentration.

Figure 3:
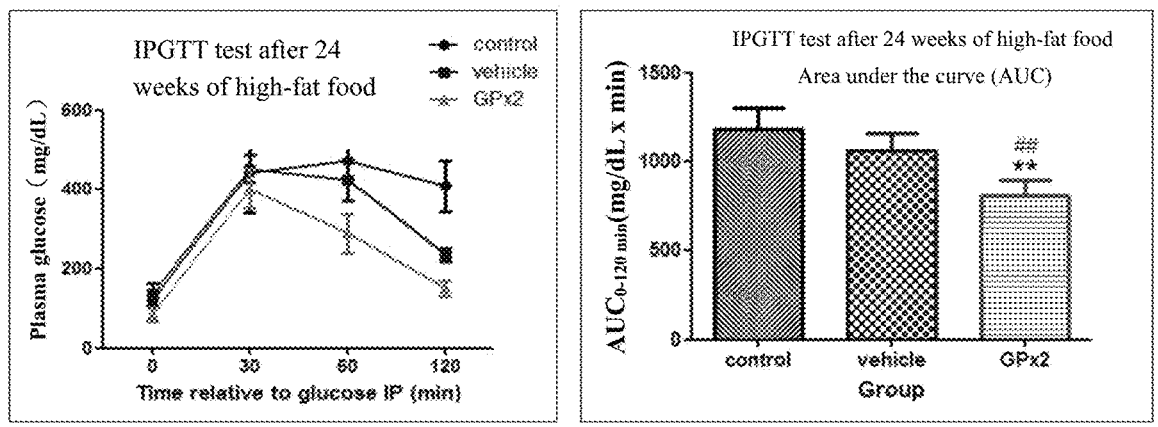
FIG. 3 shows the IPGTT results of the mice after a high-fat food; 3A: the IPGTT results of 24 weeks of high-fat food together with GPx2 over-expression plasmid; 3B: the IPGTT results, the GPx2 over-expressing plastid is administered after type II diabetes is induced by 16 weeks of high-fat food (**: p<0.01 compared to the control group; ##: p<0.01 compared to the vehicle).
Figure 3:
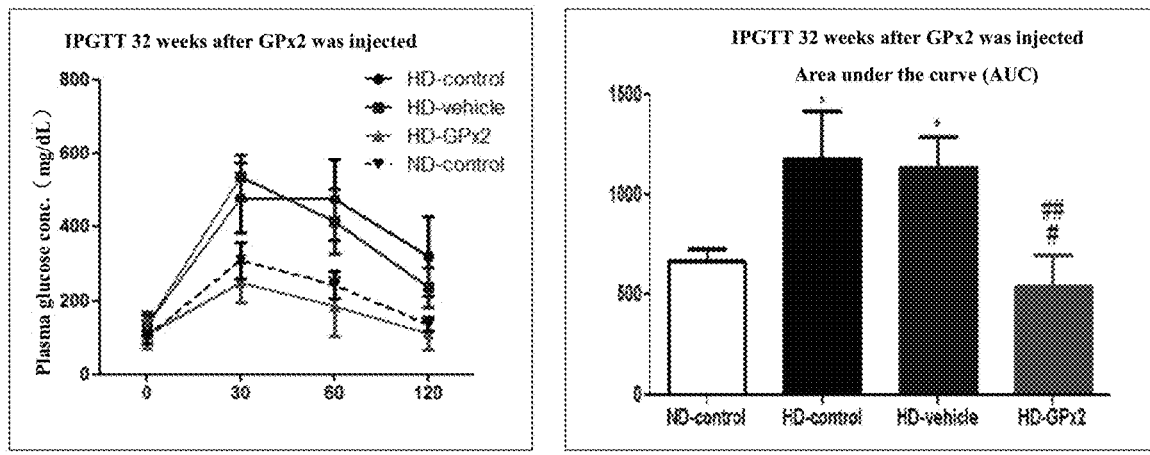

The results are shown in FIG. 3A, after the mice were fed with high-fat food and simultaneously administered with the GPx2 over-expressing plasmid via the tail vein for 24 weeks, glucose tolerance was tested, the mice administered with the GPx2 over-expressing plasmid had a better glucose metabolism condition. As shown in FIG. 3B, after diabetic mice, were successfully induced by a high-fat food for 16 weeks, and 32 weeks after the GPx2 over-expressing plasmids was administered via the tail vein, the results of the intraperitoneal glucose tolerance test (IPGTT) showed that GPx2 was able to improve the carbohydrate metabolism disorder effectively, and the mice administered with GPx2 over-expressing plastid showed a better carbohydrate metabolism condition, comparable to the diabetes-free mice fed with a normal food.

Immunohistochemical Analysis

The paraffin-embedded liver tissues were cut into 4 μm sections, microwaved at 100° C. for 30 minutes, and non-specific reactions were blocked. The sections were cultured with primary antibodies at 4° C. overnight, then rinsed twice with PBS containing 0.2% Tween 20 for 10 minutes. The sections were incubated with biotinylated secondary antibodies for one hour and then rinsed twice with PBS containing 0.2% Tween 20 for 10 minutes. Finally, the sections were stained to observe the expression of various proteins.

Patient Recruitment 48 patients suffering from the hepatitis C were recruited and categorized according to each individual's oral glucose tolerance test and glycated hemoglobin (as shown in Table 1), 19 of them were patients having normal blood glucose, 11 of them were patients with abnormal glucose tolerance, and 18 of them were type II diabetes patients.

TABLE 1

Groups of hepatitis patients

| Diagnosis | Fasting blood glucose | Blood glucose 2 hours after oral administration of glucose | glycated hemoglobin |
|---|---|---|---|
| Normal blood glucose | <110 mg/dL and | <140 mg/dL and | <5.7 |
| Abnormal glucose tolerance | 110-126 mg/dL or | 140-200 mg/dL or | 5.7-6.5 |
| Type II diabetes | >126 mg/dL or | >200 mg/dL or | >6.5 |

Virus Typing Analysis

Each patient took virus typing analysis to confirm viral genotype and virus quantitative analysis, and 5 patients with normal blood glucose, 3 patients with abnormal glucose tolerance, and 3 patients suffering from type II diabetes who had never taken insulin or oral blood glucose-lowering drugs were randomly selected as samples to perform gene chip assays to screen candidate genes, other samples were used as the validation group for verifying the candidate genes. The basic information of these two sample groups is shown in Table 2.

TABLE 2

| | Normal | Prediabetes | Diabetes | p Value |
|---|---|---|---|---|
| Gender (Male/Female) | 4/10 | 6/2 | 10/5 | 0.0489 |
| Age (Standard Deviation) | 57.3(13.2) | 56.8(9.2) | 53.9(8.2) | 0.6586 |
| BMI (Standard Deviation) | 25.2(2.5) | 25.3(2.8) | 26.4(4.2) | 0.6020 |
| GOT (IU/L, Standard Deviation) | 118.5(71.1) | 103.9(32.3) | 108.5(47.1) | 0.8291 |
| GPT (IU/L, Standard Deviation) | 166.5(70.0) | 149.4(30.3) | 159.4(68.8) | 0.8482 |
| APRI (Standard Deviation) | 2.0(13) | 1.6(0.7) | 2.1(1.5) | 0.7341 |
| 0 minute-AC SUGAR (mg/dL, Standard Deviation) | 84.4(8.0) | 91.7(10.2) | 121.8(29.9) | <0.0001 |
| 120 minutes-AC SUGAR (mg/dL, Standard Deviation) | 128.5(29.5) | 125.3(31.5) | 255.6(76.9) | <0.0001 |
| 0 minute-AC Insulin (μIU/mL, Standard Deviation) | 4.9(2.9) | 7.8(7.1) | 18.1(5.4) | 0.0300 |
| HbA1C (%, Standard Deviation) | 5.3(03) | 5.8(0.1) | 7.0(09) | <.0001 |

Liver Section

Figure 4:
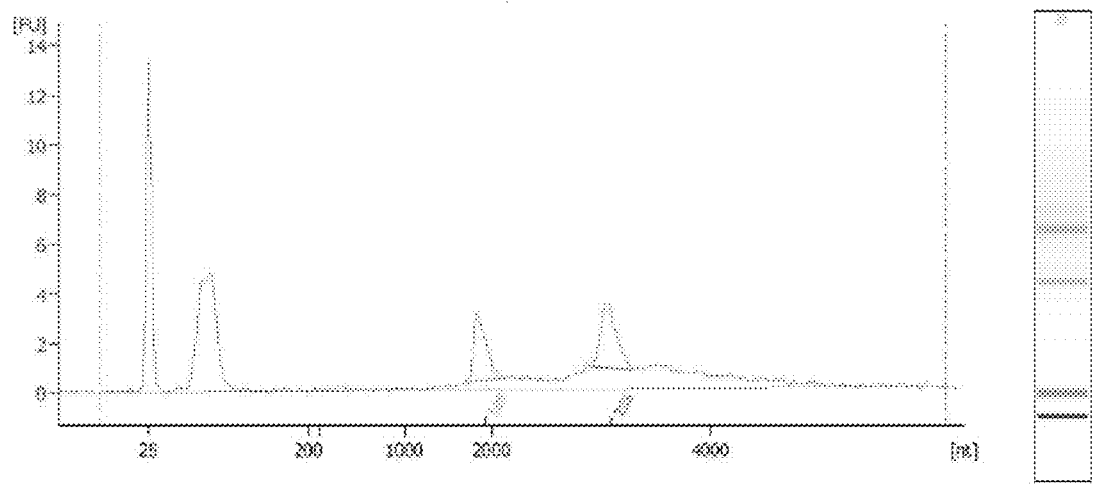
FIG. 4 shows the results that confirm the integrity of RNA and cDNA of the histological sections of the liver tissues from patients suffering from the hepatitis C; 4A: the RNA concentration and integrity confirmation map; 4B: the cDNA integrity confirmation map.
Figure 4:
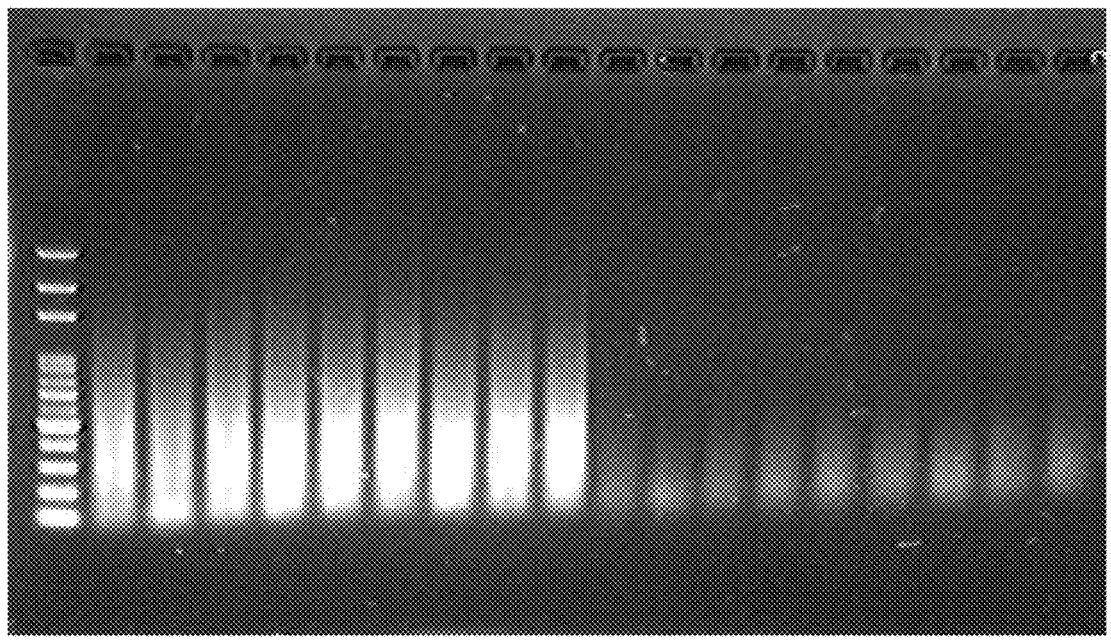

Liver sections of each patient were collected, RNA was extracted respectively, RNA concentrations were measured, and then individually converted to cDNA to confirm the integrity. The results are shown in FIG. 4.

Whole Genome Expression Detection

Figure 5:
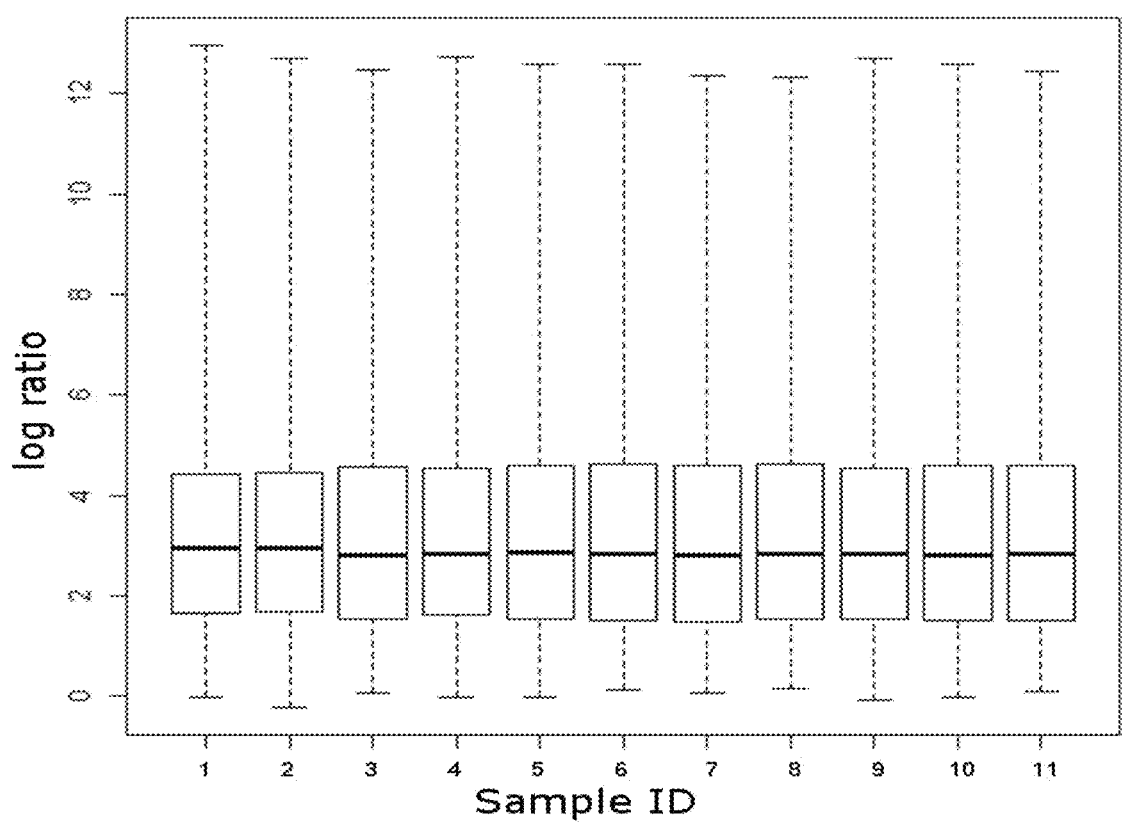
FIG. 5 is a graph showing the results of a whole genome expression detection by a microarray chip assay.

Whole genome expression detection was performed by using microarray chip assays to normalize all chip results, as shown in FIG. 5.

Then gene expression variations were analyzed. Using a 1.5-fold variation as a threshold, genes with expression variations were selected. When patients with abnormal glucose tolerance were compared to those with normal blood glucose, the expressions of 81 genes were increased, and the expressions of 77 genes were decreased; when patients suffering from type II diabetes were compared to those with normal blood glucose, the expressions of 161 genes were increased and the expressions of 99 genes were decreased.

Gene network analysis: When patients with abnormal glucose tolerance were compared to patients suffering from type II diabetes, the functions of the genes with expression variations were lipid metabolism, molecular transport, small molecule biochemistry, vitamin and mineral metabolism, etc. The results are shown in Table 3.

TABLE 3

| Description | p Value | Number of molecules |
|---|---|---|
| Abnormal glucose tolerance group and normal control group | | |
| Lipid metabolism | 2.44E−13-6.33E−03 | 47 |
| Molecular transport | 2.44E−13-6.33E−03 | 35 |
| Small molecule biochemistry | 2.44E−13-6.33E−03 | 52 |
| Vitamin and mineral metabolism | 3.24E−12-5.08E−03 | 16 |
| Cell growth and proliferation | 2.17E−06-5.63E−03 | 38 |
| Type II diabetes patients and normal control group | | |
| Lipid metabolism | 1.97E−23-1.00E−02 | 59 |
| Small molecule biochemistry | 1.97E−23-1.00E−02 | 64 |
| Vitamin and mineral metabolism | 1.97E−23-1.00E−02 | 32 |
| Molecular transport | 8.15E−09-1.00E−02 | 37 |
| Nucleic acid metabolism | 2.27E−08-1.00E−02 | 11 |

Figure 1B:
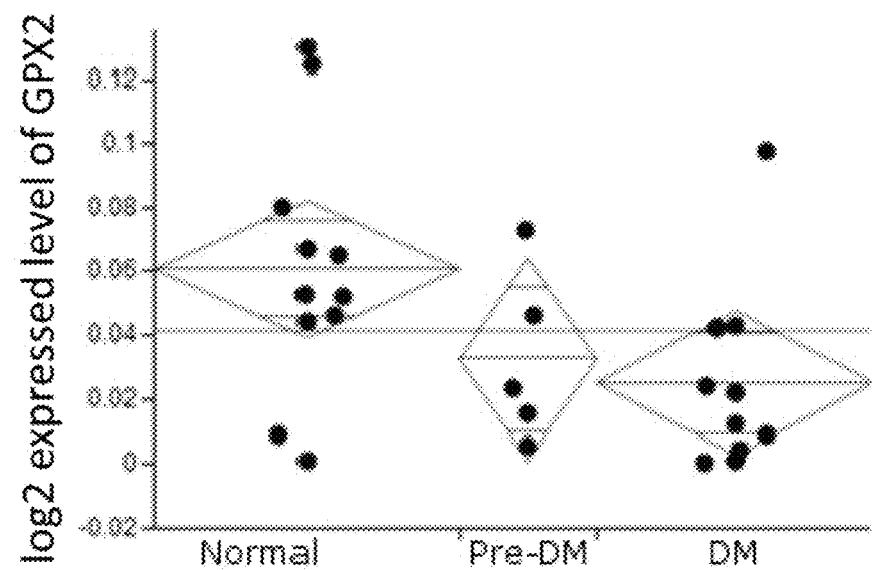

Significantly different candidate genes of GPx2 were obtained after the results of the patients having abnormal glucose tolerance were compared with the results of those who suffer from type II diabetes: when GPx2 was analyzed by qPCR, it was found that GPx2 varied in different degrees depending on the degree of variation in glucose tolerance, as shown in FIG. 1A. When the samples of the validation group were tested by qPCR, it showed that GPx2 still maintained significant variations, and depending on the variations in glucose tolerance, the expression level of GPx2 gene was also decreased, as shown in FIG. 1B.

Gene Network Analysis

Based on the predictions of the gene network analysis, GPx2 was closely related to genes related to fatty acid oxidation, glucose tolerance, glucose uptake, and gluconeogenesis.

The Role of GPx2 in Carbohydrate Metabolism

The role of GPx2 in carbohydrate metabolism was confirmed by cell experiments. Through inhibiting the expression of GPx2, Hepatitis C virus (HCV) allowed HCV to cause carbohydrate metabolism disorder in liver cells (reducing glucose transport and increasing gluconeogenesis), and by increasing the expression of GPx2, the abnormal glucose metabolism caused by HCV was significantly improved.

Figure 6:
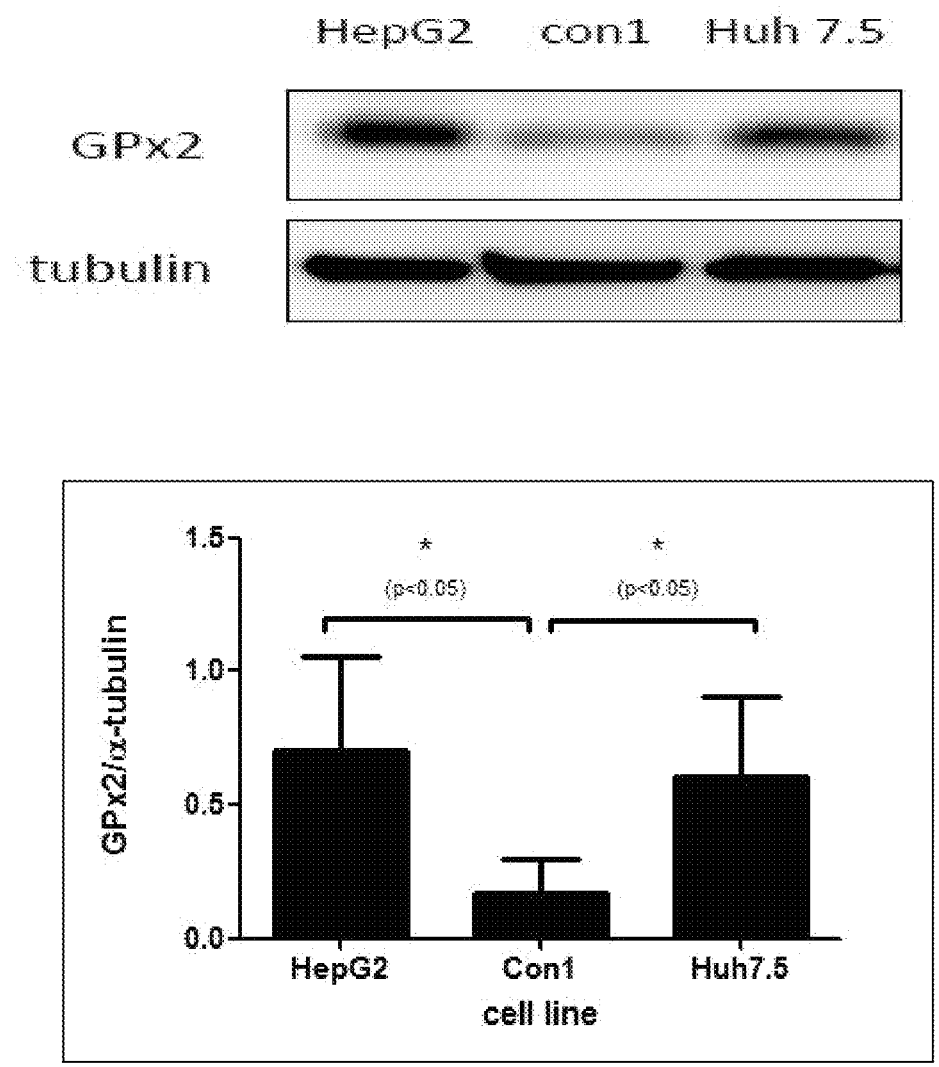
FIG. 6 shows the expression of GPx2 in HepG2, Con1, Huh7.5 cell lines.

Through plasmid transfection and immunoblotting experiments, it was found that the expression of GPx2 in the cells (Con1 cells) having HCV type 1b replicon-related genes was significantly decreased as compared to the cells (HepG2 and Huh7.5) without HCV-related genes, as shown in FIG. 6.

Figure 7:
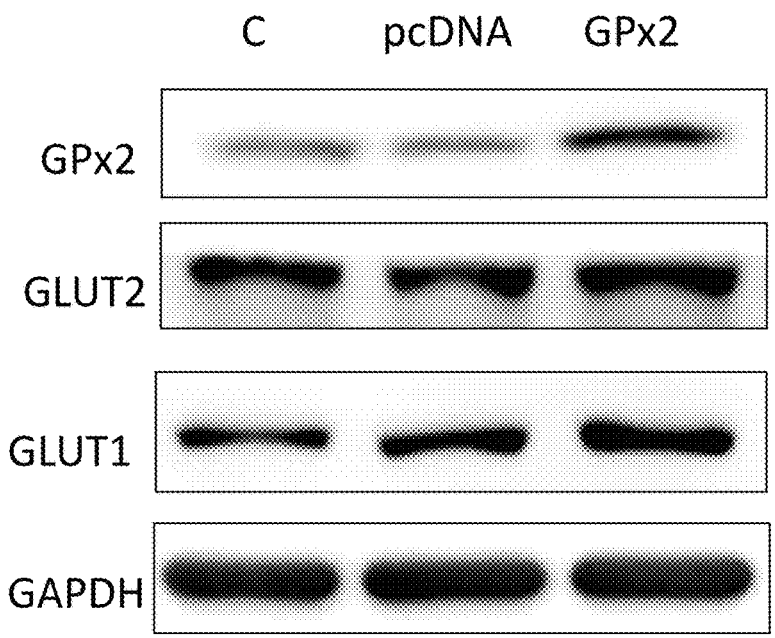
FIG. 7 shows the expression of GLUT1 and GLUT2 in the Con1 cell line administered with the GPx2 over-expressing plasmid (*: p<0.05 compared to the vehicle; **: p<0.01 compared to the vehicle; #: p<0.05 compared to the control group).
Figure 7:
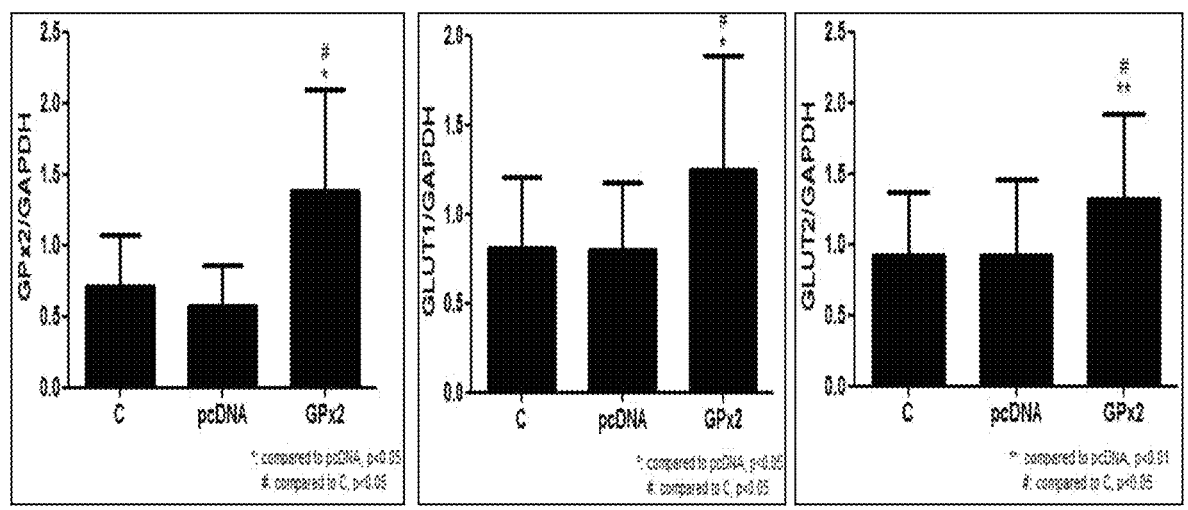

Previous studies had shown that HCV was able to decrease the expression level of GLUT in the cells (Con1) having the expression of HCV related genes. Therefore, after the present invention increased the expression level of GPx2 by giving the GPx2 over-expressing plasmid, it was found that the expression of GLUT was significantly increased, indicating that GPx2 was able to improve the ability of the cells to transport glucose, as shown in FIG. 7.

Figure 8:
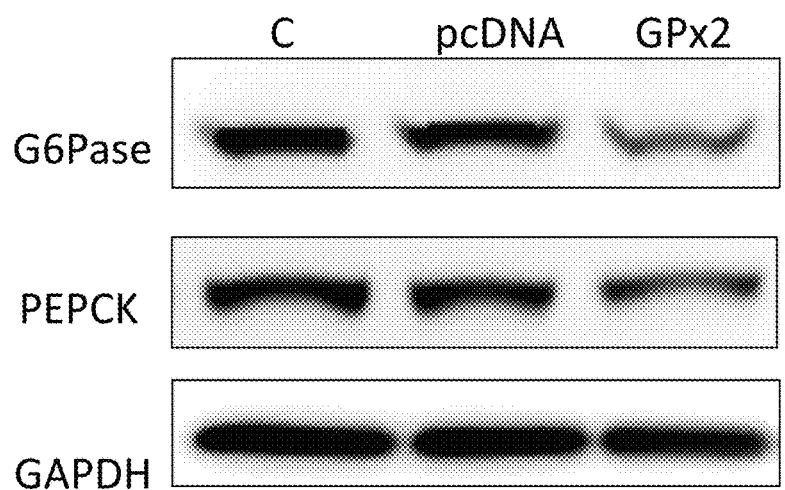
FIG. 8 shows the expression of G6Pase and PEPCK in the Con1 cell administered with the GPx2 over-expressing plasmid (*: p<0.05 compared to the vehicle; **: p<0.01 compared to the vehicle; ##: p<0.01 compared to the control group; ###: p<0.001 compared to the control group).
Figure 8:
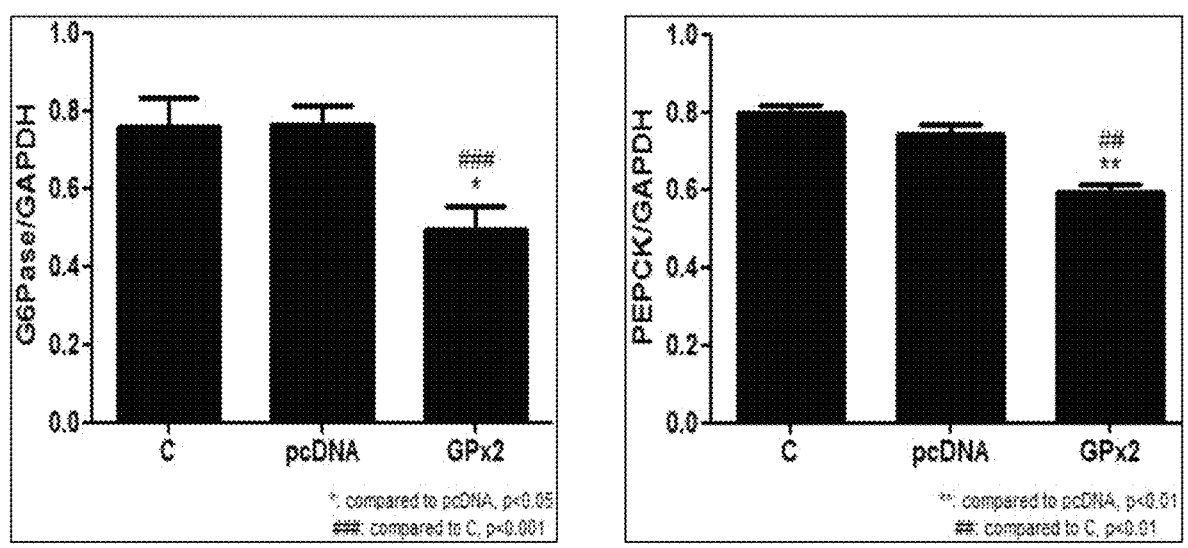

It had been reported that HCV was able to increase the expression level of gluconeogenesis-related genes (G6PC (G6Pase) and PEPCK) in the cells (Con1) having the expression of HCV-related genes. Therefore, after the present invention increased the expression level of GPx2 by giving GPx2 over-expressing plasmid, the expressions of G6PC (G6Pase) and PEPCK were significantly decreased to inhibit gluconeogenesis in the cells, as shown in FIG. 8.

Figure 9:
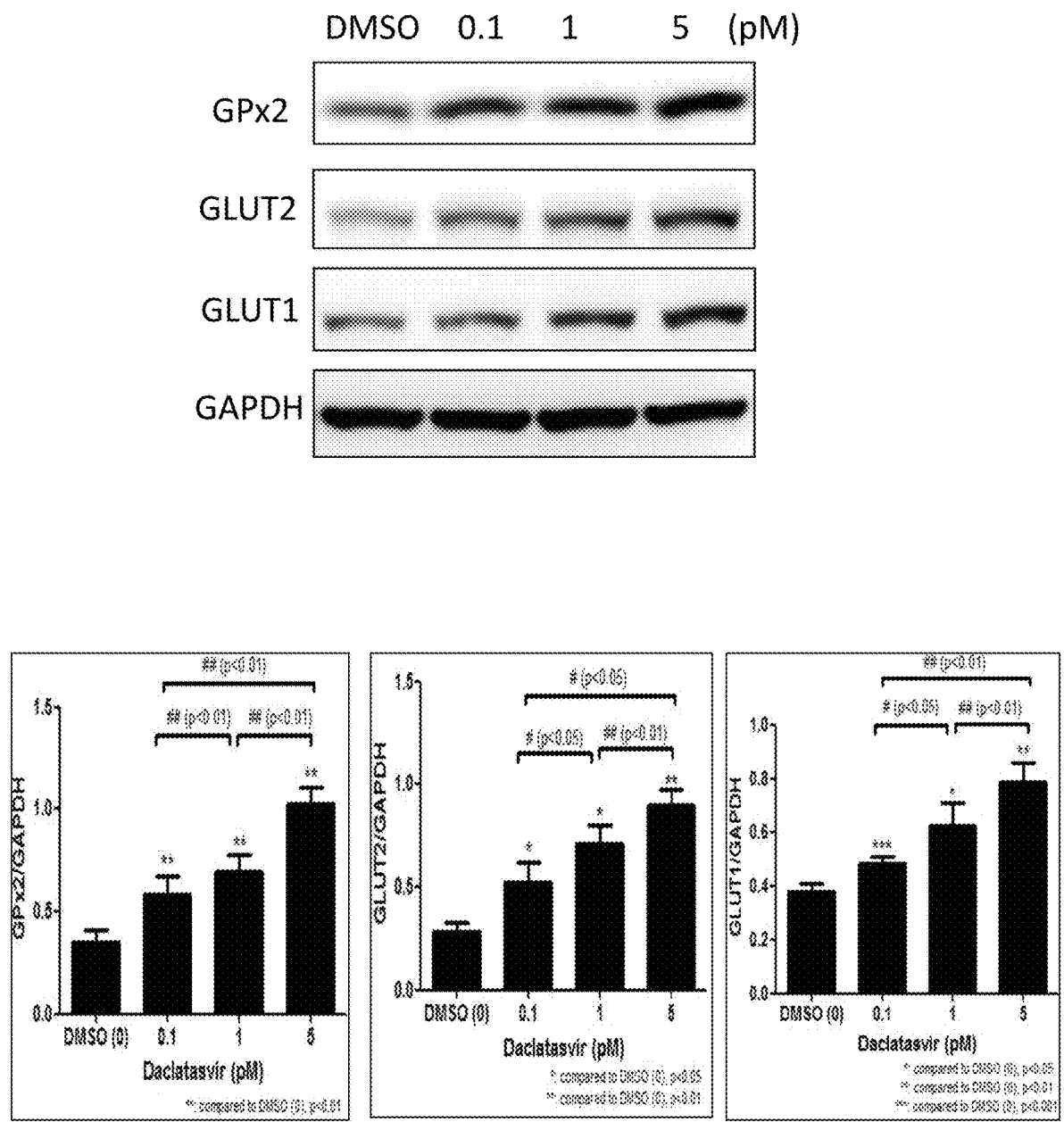
FIG. 9 shows the expression of GPx2, GLUT1 and GLUT2 in the Con1 cell lines administered with different concentrations of HCV-specific viral inhibitors (Daclatasvir) (*: p<0.05 compared to DMSO (Daclatasvir concentration 0 pM); : p<0.01; *: p<0.001; compared to the effect of different concentrations of Daclatasvir, #: p<0.05; ##: p<0.01).
Figure 10:
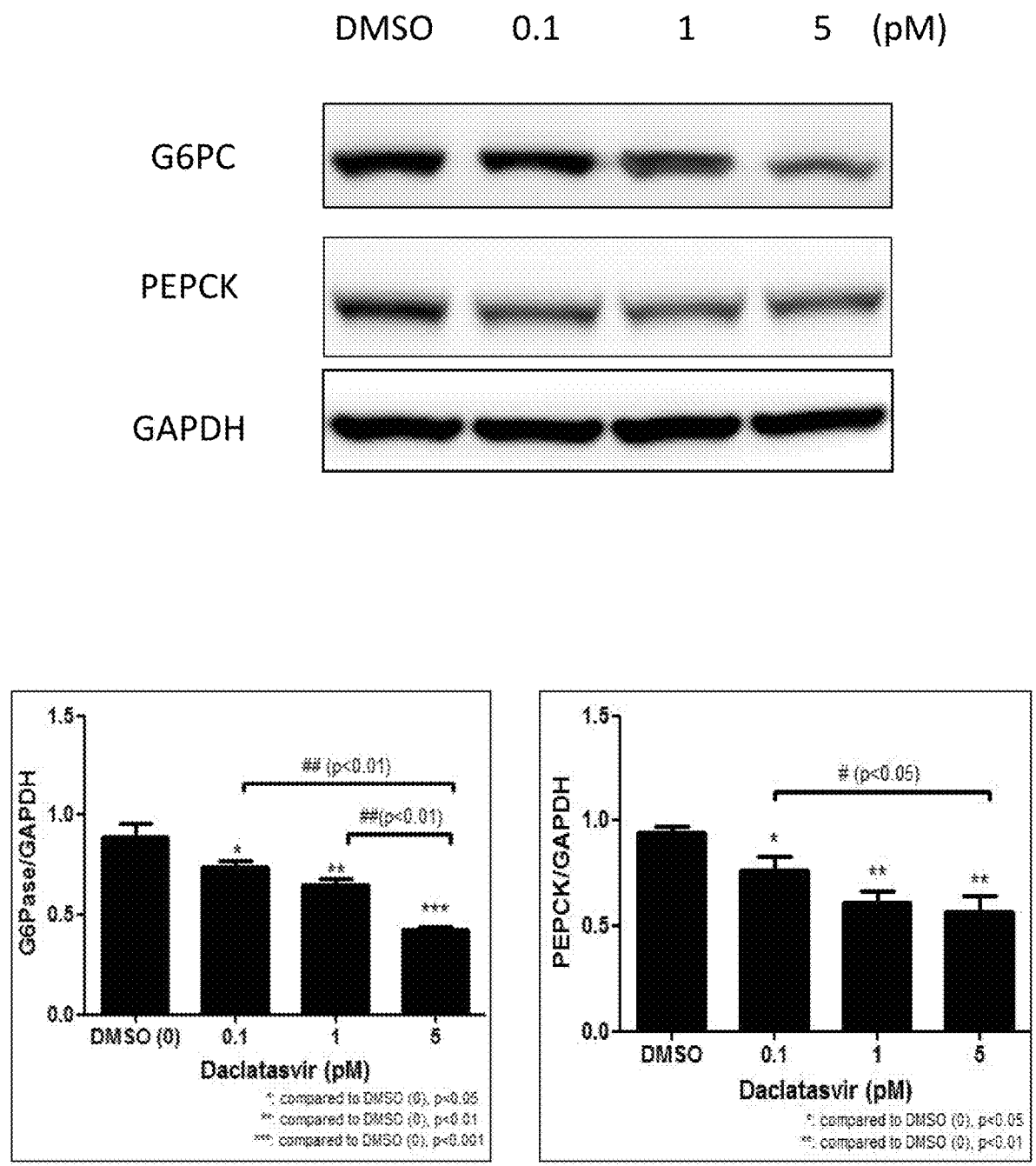
FIG. 10 shows the expression of G6PC (G6Pase) and PEPCK in the Con1 cell lines administered with different concentrations of the HCV-specific viral inhibitor (Daclatasvir) (compared to DMSO (Daclatasvir concentration is 0 pM); *: p<0.05; p<0.01; ***: p<0.001; compared to the effect of different concentrations of Daclatasvir, #: p<0.05; ##: p<0.01).

After the Con1 cells were treated with the HCV-specific viral inhibitor (Daclatasvir) and detected by Western blotting, it was found that as the concentration of the inhibitor increased, the amount of virus decreased to increase the expression of GPx2 and GLUT on concentration-dependent manner, as shown in FIG. 9. The gluconeogenesis-related proteins G6PC (G6Pase) and PEPCK were also down-regulated by Daclatasvir in a concentration-dependent manner, as shown in FIG. 10.

Figure 11:
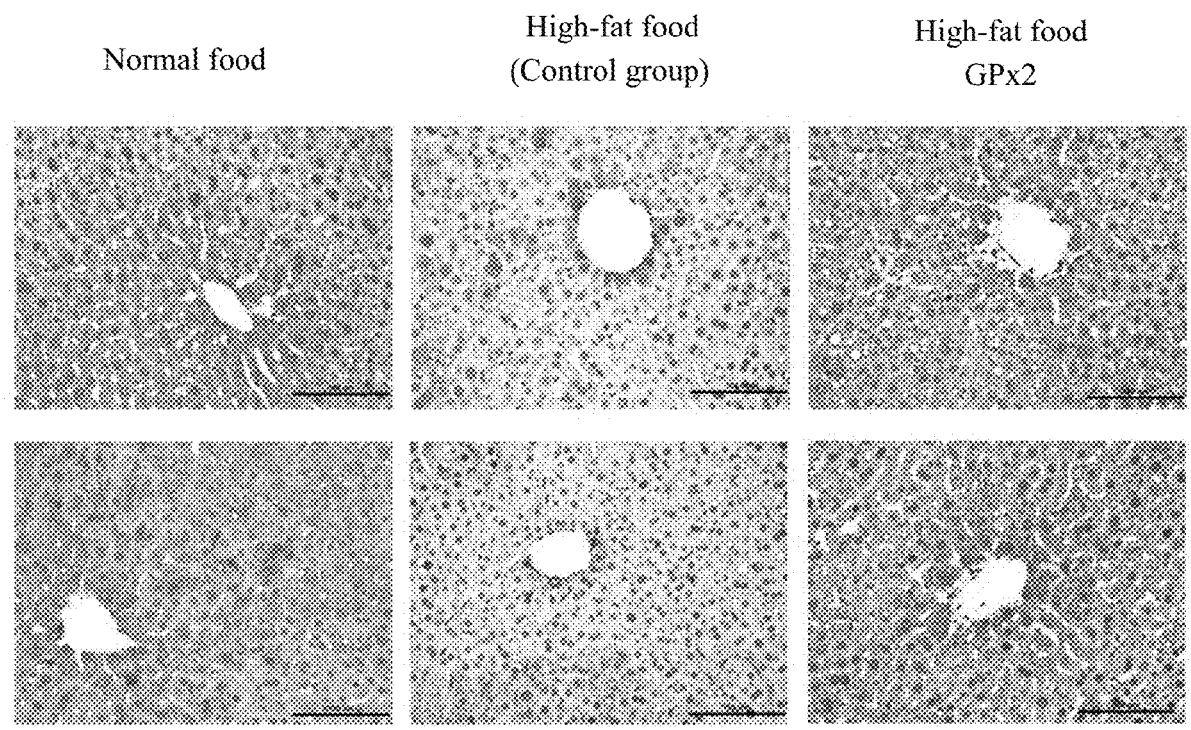
FIG. 11 shows the expression of GPx2 in the liver in the mice with high-fat food for 24 weeks.
Figure 12:
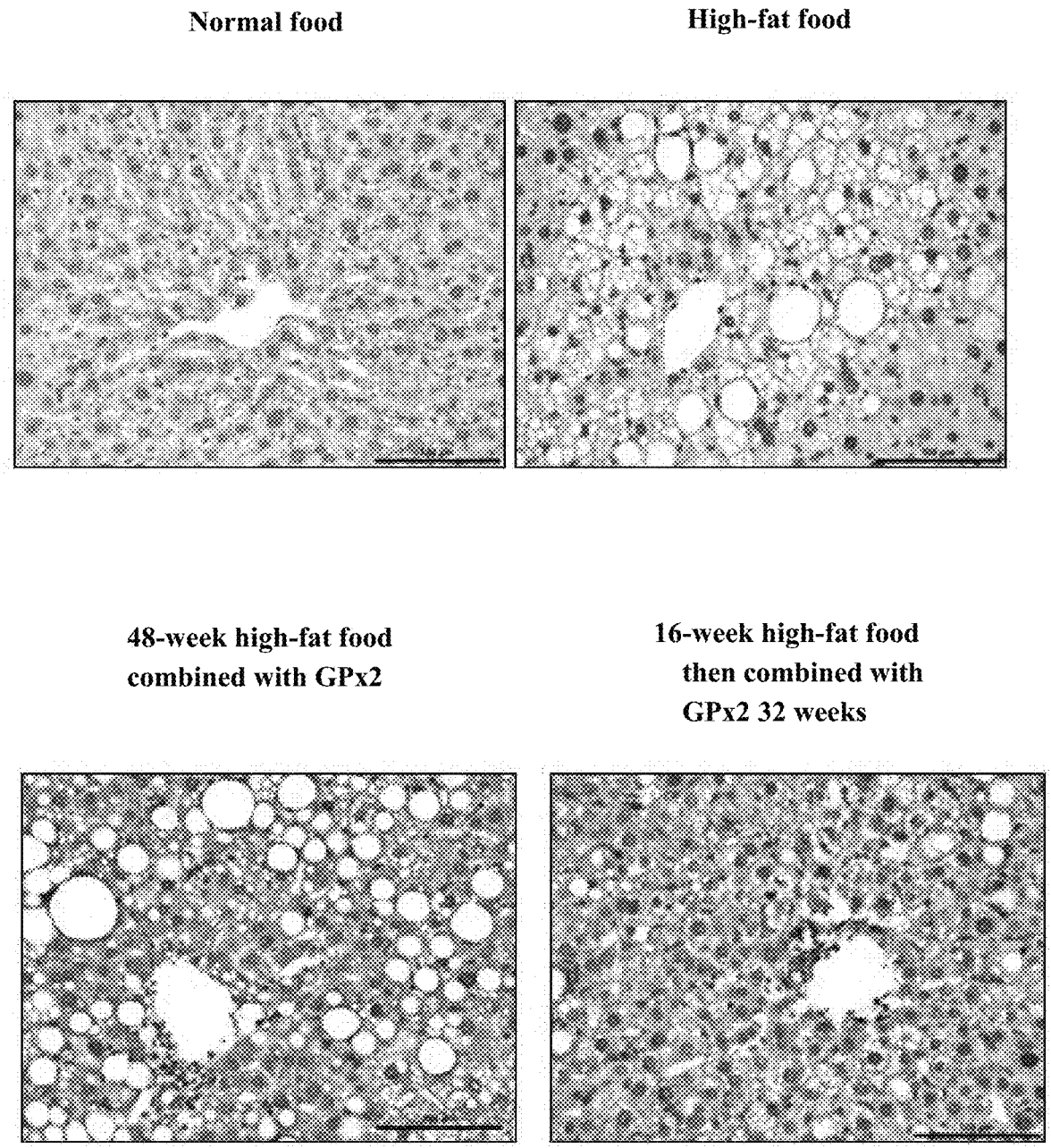
FIG. 12 shows the expression of GPx2 in the liver of the mice with high-fat food for 48 weeks.
Figure 13:
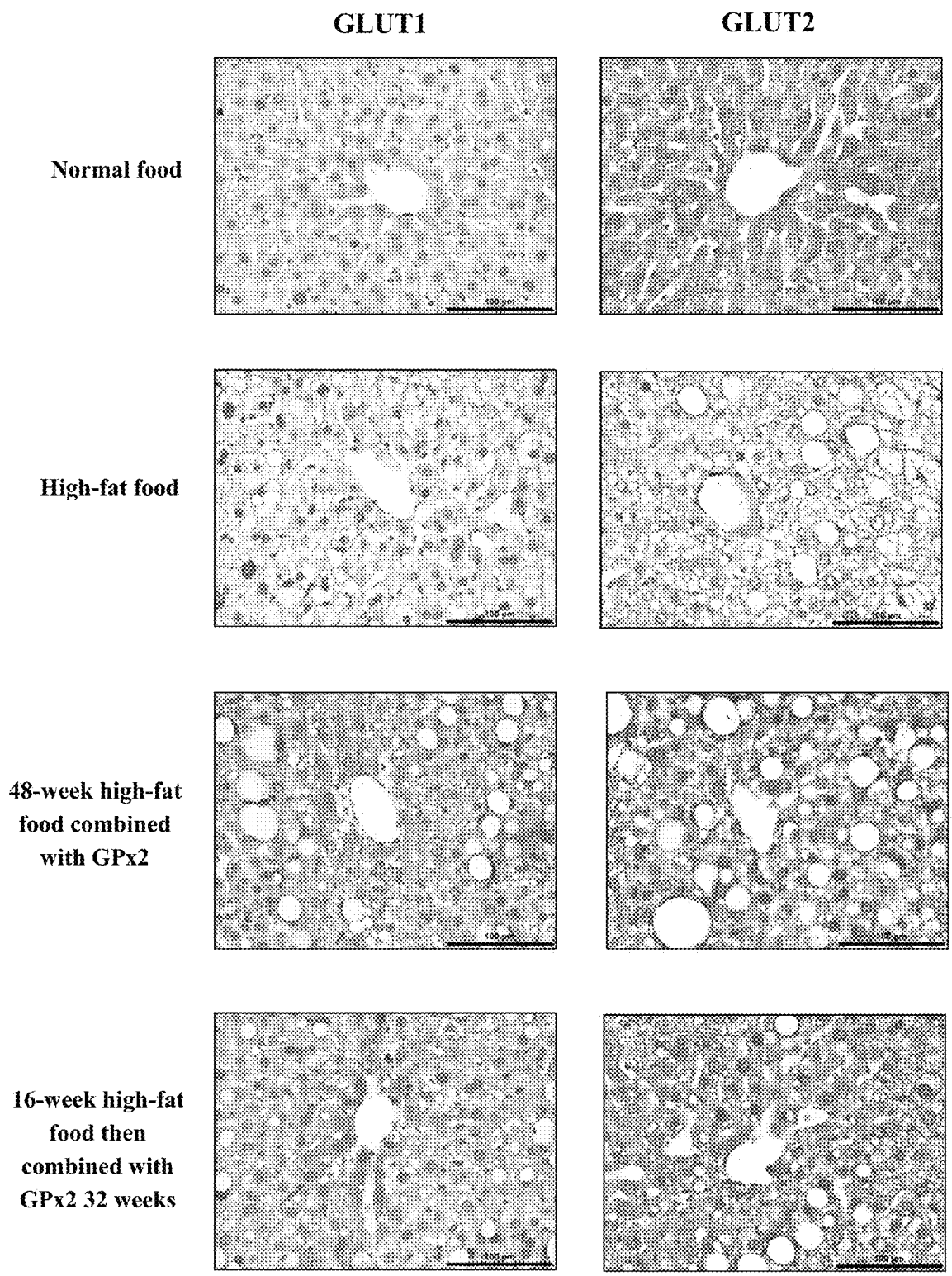
FIG. 13 shows the expression of GLUT in the liver of the mice with high-fat food for 48 weeks.
Figure 14:
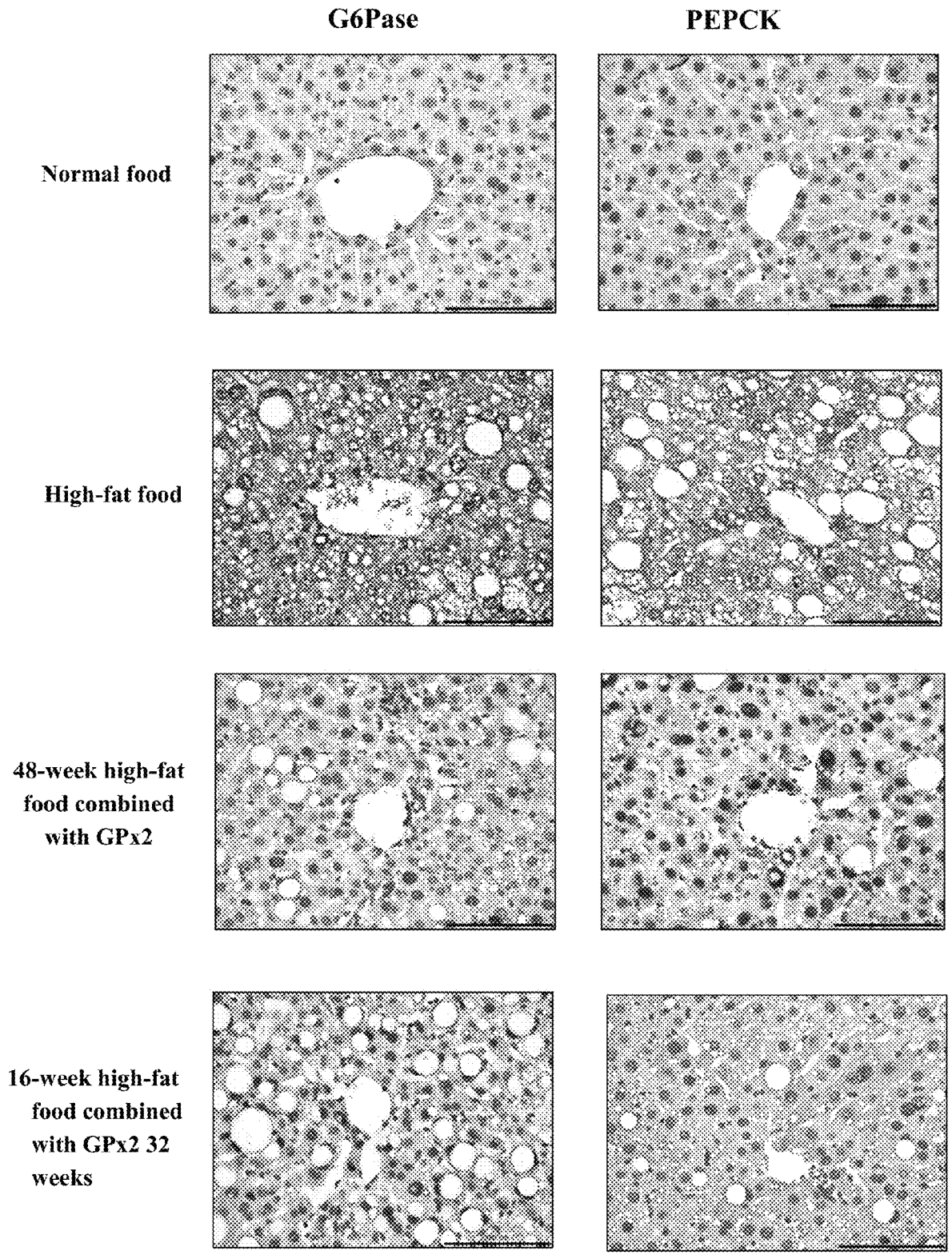
FIG. 14 shows the expression of the proteins related to gluconeogenesis in the liver of the mice with high-fat food for 48 weeks.
Figure 15:
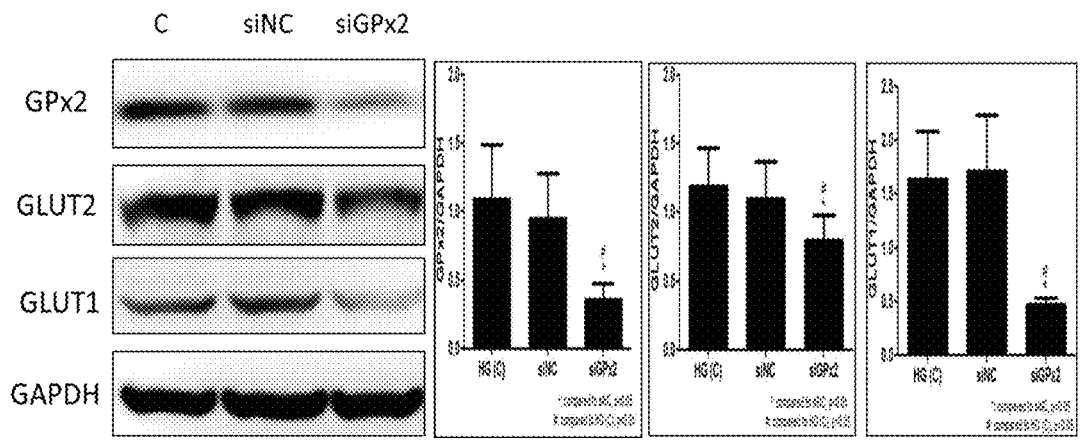
FIG. 15 shows the expression of GLUT2, G6PC (G6Pase) and PEPCK after the expression of GPx2 is inhibited by GPx2 siRNA treatment.
Figure 15:
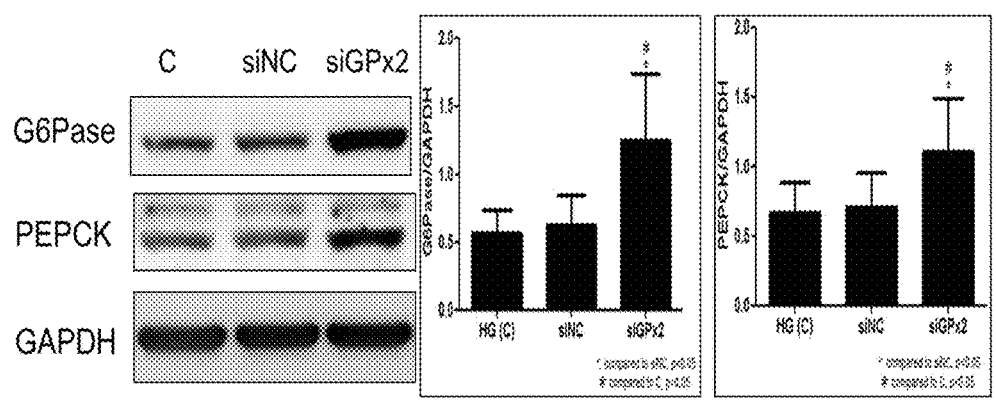
Figure 15:
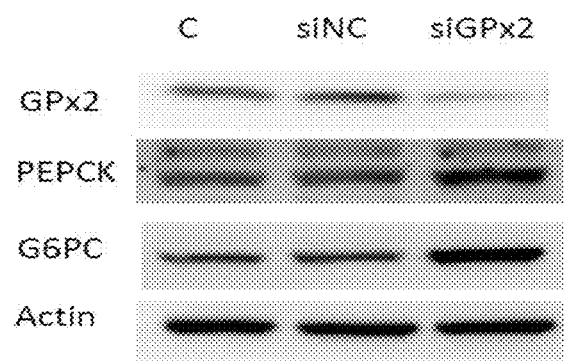

Through the immunohistostaining results, it was found that the expression of GPx2 was decreased in high-fat food-induced diabetic mice; and after the GPx2 over-expressing plasmid was administered, the expression level of GPx2 was increased, as shown in FIG. 11. In the experiments of the 48-week high-fat food, the expression of GPx2 was also significantly increased, as shown in FIG. 12. The expression of GLUT was decreased in high-fat food-induced diabetic mice; and the expression of GLUT was increased after the GPx2 over-expressing plasmid was administered, as shown in FIG. 13. The expression level of G6PC (G6Pase) and PEPCK in high-fat food-induced diabetic mice was increased, and the expression level of G6PC (G6Pase) and PEPCK was decreased after the GPx2 over-expressing plasmid was administered, as shown in FIG. 14.

What is claimed is:

1. A method for preventing or treating type II diabetes in a subject at high risk of developing type II diabetes or suffering from type II diabetes, comprising administering to the subject at high risk of developing type II diabetes or suffering from type II diabetes a composition comprising an effective amount of a plasmid comprising a nucleic acid molecule encoding glutathione peroxidase 2 (GPx2) and a pharmaceutically acceptable carrier.

2. The method of claim 1, wherein the type II diabetes is caused by hepatitis C virus infection or a high-fat diet.

3. The method of claim 1, wherein the subject is a human.

* * * * *